Dec. 13, 1960 E. S. BOERNER Plant Pat. 2,000
ROSE PLANT
Filed March 1, 1960
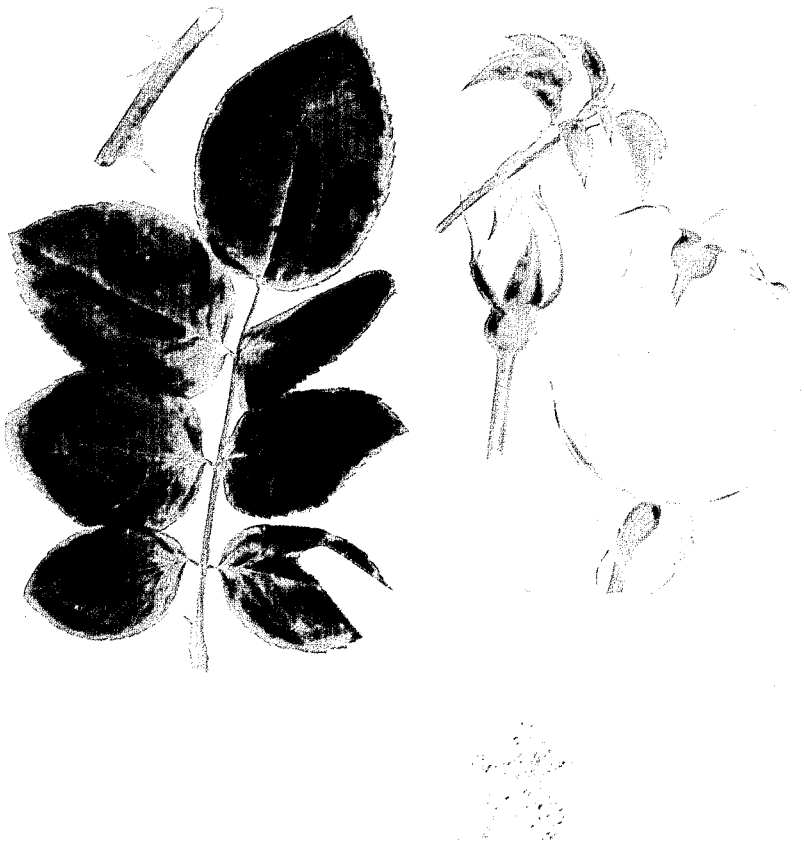
Inventor.
E. S. Boerner
By: Robb & Robb
Attorneys.

United States Patent Office

Plant Pat. 2,000
Patented Dec. 13, 1960

2,000

ROSE PLANT

Eugene S. Boerner, Newark, N.Y., assignor to Jackson & Perkins Company, Newark, N.Y., a corporation of New York Filed Mar. 1, 1960, Ser. No. 12,242

1 Claim. (Cl. 47—61)

The present invention relates to a new and distinct variety of rose plant of the hybrid tea class, which was originated by me by crossing the variety "Golden Masterpiece" (Plant Patent No. 1,284) with the variety "Kate Smith" (Plant Patent No. 1,317).

The primary objective of this breeding was to produce a new rose variety which bears firmer and more high-centered flowers, combined with the excellent growth habits and foliage of the parent variety "Golden Masterpiece." This objective was fully achieved, as evidenced by the following unique combination of characteristics which are outstanding in the new variety and which distinguish it from its parents, as well as from all other varieties of which I am aware:

(1) Tall, vigorous shoots on which the flowers are borne;

(2) Distinctive thorns which have straight points and large, flat bases;

(3) Flowers which are of exceptionally large size for this particular color range;

(4) A high-centered hybrid tea flower form; and (5) A distinctive color tonality of the flowers corresponding to Light Orange-Yellow, lightly overcast with Grenadine Pink.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Golden Masterpiece."
*Pollen parent.*—"Kate Smith."

Classification:
*Botanic.*—"Hybrid tea."
*Commercial.*—"Hybrid tea."

*Flower*

(Observations made from specimens grown in a greenhouse at Newark, New York, in the early afternoon and during the latter part of the month of October.)

Blooming habit: Recurrent—continuous.

Bud:
*Size.*—Very large.
*Form.*—Long; is not affected by wet or hot weather.
*Color.*—When sepals first divide—Light Coral Red, Plate 13, with lower half of petals lightly overcast with Empire Yellow, Plate 4. When petals begin to unfurl—Light Orange-Yellow, Plate 3. When half-blown: inside of petals—Flame Scarlet, Plate 2, with outer edge of petals lightly overcast with Deep Chrome, Plate 3; reverse of petals—Light Orange-Yellow, Plate 3, with outer edge of petals lightly overcast with Bittersweet Pink, Plate 2.

*Sepals.*—Slightly branched; curl back when petals begin to unfurl. Color: inside—Pale Fluorite Green, Plate 32, outside—Spinach Green, Plate 5.
*Calyx.*—Color—Spinach Green, Plate 5. Shape—apple. Size—large. Aspect—smooth. Odor when rubbed—none.
*Peduncle.*—Length—medium. Aspect—smooth. Strength—erect; heavy. Color—Oil Green, Plate 5.
*Opening.*—Opens up well; is not affected by adverse weather conditions.

Bloom:
*Size.*—Very large. Average size when fully expanded—6 inches.
*Borne.*—Both singly and several together.
*Stems.*—Long; strong.
*Form (when first open.)*—High-centered. Permanence—retains its form to the end.
*Petalage.*—Double (full but open center). Number of petals under normal conditions—from 45 to 50.
*Color.*—Center of flower—Light Orange-Yellow, Plate 3, lightly overcast with Grenadine Pink, Plate 2. Outer petals—Pale Orange-Yellow, Plate 3, with edge of petals lightly overcast with Grenadine Pink, Plate 2. Base of petals (aiglet)—Lemon Chrome, Plate 4. Inside of petals—Light Orange-Yellow, Plate 3, lightly overcast with Grenadine Pink, Plate 2. Reverse of petals—Pale Yellow-Orange, Plate 3, lightly overcast with Seashell Pink, Plate 14. General tonality from a distance—Light Orange-Yellow, Plate 3, lightly overcast with Grenadine Pink, Plate 2.
*Discoloration.*—General tonality at end of first day—Light Orange-Yellow, Plate 3, lightly overcast with Grenadine Pink, Plate 2. Second day—Light Orange-Yellow, Plate 3, lightly overcast with Grenadine Pink, Plate 2. Third day—Pale Orange-Yellow, Plate 3, lightly overcast with Grenadine Pink, Plate 2.

Petals:
*Texture.*—Thick; is not affected by wet or hot weather.
*Appearance.*—Inside—satiny. Outside—shiny.
*Form.*—Oval.
*Arrangement.*—Informal (with "rags" in center).
*Petaloids in center.*—Few; large.
*Persistence.*—Drop off cleanly.
*Fragrance.*—Strong. Nature—tea (average hybrid tea scent).
*Lasting quality.*—On the plant—very long. As cut flower—very long.

*Genital organs*

Stamens, anthers: Medium size; many; mixed with petaloids. Color—Salmon-Orange, Plate 2.
Stamens, filaments (threads): Long. Color—Pale Orange-Yellow, Plate 3.
Pollen: Color—Orange-Pink, Plate 2.
Styles: Columnar; uneven length; medium length; thin.
Stigmas: Color—Baryta-Yellow, Plate 4.
Ovaries: All enclosed in calyx.
Hips: None.
Seeds: None.

*Plant*

Form: Bush.
Growth: Very vigorous; upright; tall.
Foliage: Compound of 5 to 7 leaflets.

*Size.*—Very large.

*Quantity.*—Abundant.

*Color.*—New foliage: upper side—Parrot Green, Plate 6, with serrations Oxblood Red, Plate 1; under side—Oil Green, Plate 5, lightly overcast with Morocco Red, Plate 1. Old foliage: upper side—Varley's Green, Plate 18; under side—Light Elm Green, Plate 17.

*Shape.*—Oval pointed.

*Texture.*—Upper side—leathery; glossy. Under side—smooth.

*Ribs and veins.*—Ordinary.

*Edge.*—Serrated (saw-toothed).

*Serration.*—Both double and single; large.

*Leaf stem.*—Color—Light Bice Green, Plate 17. Under side—prickly.

*Stipules.*—Long; bearded.

Wood:

*New wood.*—Color—Oil Green, Plate 5. Bark—smooth.

*Old wood.*—Color—Cress Green, Plate 31. Bark—smooth.

Thorns:

*Thorns.*—Quantity: on main stalks from base—ordinary; on laterals from stalk—ordinary. Form—flat base; medium length; straight. Color (when young)—Light Yellowish-Olive, Plate 30. Position—irregular.

*Prickles.*—Quantity: on main stalks—none; on laterals—none.

*Short needles.*—Quantity: on main stalks—none. on laterals—none.

I claim:

A new and distinct variety of rose plant of the hybrid tea class, substantially as herein shown and described, characterized particularly as to novelty by the unique combination of tall and vigorous shoots on which the flowers are borne, distinctive thorns which have straight points and large, flat bases, exceptionally large flowers, a high-centered hybrid tea flower form, and a distinctive general color tonality of the flowers corresponding to Light Orange-Yellow, lightly overcast with Grenadine Pink.

No references cited.